United States Patent [19]
Terhune

[11] Patent Number: 5,289,436
[45] Date of Patent: Feb. 22, 1994

[54] ULTRASONIC WAVEGUIDE

[75] Inventor: James H. Terhune, San Jose, Calif.

[73] Assignee: General Electric Company, San Jose, Calif.

[21] Appl. No.: 965,595

[22] Filed: Oct. 22, 1992

[51] Int. Cl.⁵ .............................................. H04B 11/00
[52] U.S. Cl. ..................... 367/191; 73/644; 128/663.01; 381/154; 181/400
[58] Field of Search ................ 128/662.03, 663.01, 128/24 EL, 24 AA; 73/644; 381/154; 367/140, 191; 181/400

[56] References Cited

U.S. PATENT DOCUMENTS

| | | | |
|---|---|---|---|
| 3,497,728 | 2/1970 | Ostrofsky et al. | 73/644 |
| 3,798,961 | 3/1974 | Flambard et al. | 73/644 |
| 4,563,895 | 1/1986 | Eckert | 73/644 |
| 4,722,346 | 2/1988 | Chen | 128/662.03 |
| 4,867,169 | 9/1989 | Machida et al. | 128/662.03 |
| 4,972,826 | 11/1990 | Koehler et al. | 128/663.01 |

OTHER PUBLICATIONS

Yeh et al., "Dynamics of a Cylindrical Shell System Coupled by Viscous Fluid", J. Acoust. Soc. Am., vol. 62, No. 2, 262–70 (1977).

Warburton, "Vibration of a Cylindrical Shell in an Acoustic Medium," J. Mech. Eng. Sci., vol. 3, No. 1, 69–79 (1961).

Terhune et al., "Wave Motion of a Compressible Viscous Fluid Contained in a Cylindrical Shell," Proc. ASME PV&P Conf., 231, 4–50 (1992).

*Primary Examiner*—J. Woodrow Eldred
*Attorney, Agent, or Firm*—J. S. Beulick

[57] ABSTRACT

An ultrasonic waveguide includes a fluid-tight thin-walled tube filled with a viscous, compressible fluid. One end of the tube is coupled to a transducer for transforming electrical energy into waves of ultrasonic energy which propagate the length of the tube. The other end of the tube has a window or refracting "shoe" for transmitting or refracting the propagating ultrasonic wave therethrough. The tube has a substantially constant cross section, preferably circular. The internal diameter of the preferred circular tube is in the millimeter regime, preferably from 0.25 to 1 mm. The wall material is preferably metal, plastic or metal/plastic composite.

20 Claims, 4 Drawing Sheets

ULTRASONIC WAVEGUIDE

FIELD OF THE INVENTION

This invention relates generally to non-destructive examination of material, such as metal, for voids, flaws, cracks and other defects that can be detrimental to the integrity of the material. Specifically, the invention relates to the ultrasonic inspection of nuclear and non-nuclear components at operating plants and facilities.

BACKGROUND OF THE INVENTION

Ultrasonic inspections of reactor in-vessel components are of ten performed remotely under difficult circumstances requiring complex and expensive manipulators to position one or more transducers near the surf ace of the component. The transducers then scan over a portion of the surface to image any flaws in the volume scanned. Usually, there are regions of the reactor internals that are inaccessible to the relatively large manipulator arm, limiting the ability to fully inspect, for example, some important portions of the vessel wall, in-core and control-rod-drive housings, and stub tubes.

One difficulty encountered is placement of the transducer close to, or in contact with, the inspection surface. In-vessel inspections are conducted with submersible transducers that usually require a proximate hardened electronics package for pulsing and detection purposes. Some transducers require a relatively proximate preamplifier. The design and construction of electronics packages that can withstand gamma radiation emanating f rom the reactor core has been successfully undertaken, but cost savings would result if such novel designs were unnecessary. Rather, some inexpensive and compact means of transporting the sonic energy between a central location and a remote inspection surface would simplify the design and operation of in-vessel, as well as other, inspection systems.

Ultrasonic waveguides are known which comprise thin metal rods. However, such rods are not very flexible, making them undesirable for use in inspecting components of nuclear reactors having surf aces which are difficult to access. Also, such metal rods are very inefficient due to the severe attenuation of the ultrasonic waves, especially shear mode waves, in the metal. This problem led to consideration of fluid-filled thin-walled tubes to transport ultrasonic energy.

Ultrasonic waves propagating in fluids are essentially compressive in nature. The fluid motion is parallel to the direction of propagation, just like longitudinal waves in solids. Such waves usually diverge spherically from small point-like sources, and the intensity obeys the inverse-square law. However, in the presence of a solid boundary of cylindrical shape, i.e., a duct, the waves traveling in a viscous fluid can be propagated in certain modes of differing axial symmetry. The waves are damped in time and space as they propagate, depending on the properties of the fluid and duct, the duct dimensions and the wave frequency. In fact, damping is most appreciable for shear-wave motion of the fluid, confined to the boundary layer near the solid walls.

A lengthy and in-depth analysis of the free vibration of a thin-walled cylindrical waveguide filled with a compressible viscous fluid has been performed using the linearized Navier-Stokes equations [see, L. D. Landau and E. M. Lifshitz, Fluid Mechanics, Addison-Wesley, Reading, (1959)], the fluid continuity equation and Flugge's equations of motion for thin shells [see, W. Flugge, Stresses in Shells, Springer-Verlag, Berlin, (1960)]. Unique solutions can be obtained for which the interface conditions at the waveguide inner surface can be satisfied. Formally, a characteristic equation for the system eigenvalues can be formulated and a numerical solution can be derived. [see, T. T. Yeh and S. S. Chem, "Dynamics of a Cylindrical Shell system coupled by Viscous Fluid", J. Acost. Soc. Am., Vol., 62, No. 2, 262-270 (1977) and G. B. Warburton, "Vibration of a Cylindrical Shell in an Acoustic Medium," J. Mech. Eng. Sc., Vol. 3, No. 1, 69-79 (1961).]

It can be shown that a solution exists for guided wave modes in the special case of axi-symmetric propagation. The characteristic equation can be solved numerically in this case, resulting in a dispersion equation for axial wave propagation. [See, J. H. Terhune and K. Karim-Panahi, "Wave Motion of a Compressible Viscous Fluid Contained in a Cylindrical Shell", Proc. ASME PV&P Conf., New Orleans, Vol. 231, 41-50 (1992).]

SUMMARY OF THE INVENTION

The present invention is a waveguide which utilizes the properties of wave propagation in fluid interacting with a thin-walled tube to effectively transport ultrasonic energy over substantial distances for the purpose of remote inspection. This waveguide employs traveling ultrasonic waves in specific modes of propagation at a pre-selected central frequency and bandwidth in order to produce a remote source or detector of pulsed ultrasound.

The ultrasonic waveguide of the invention also utilizes the unique properties of wave propagation in fluids in combination with transmission properties of thin shells to provide a flexible conduit for efficient transport of ultrasound around objects that would otherwise preclude access for ultrasonic inspection.

Further, the waveguide of the invention is amenable to remote pulse-echo operation, or pitch-catch, as the application requires, using standard transducers of common bandwidth and nominal frequency. In this application the energy is channeled in a direction specified by the waveguide, rather than in all directions.

Lastly, the waveguide of the invention significantly enhances the sonic intensity at the inspection location, even in the presence of absorption, in order to efficiently deliver energy to the volume being inspected.

In accordance with the preferred embodiment of the invention, the waveguide comprises a fluid-tight thin-walled tube filled with a viscous, compressible fluid. One end of the tube is coupled to transducing means for transforming electrical energy into waves of ultrasonic energy which propagate the length of the tube. The other end of the tube has means for transmitting the propagating ultrasonic wave therethrough. The tube has a substantially constant cross section, preferably circular. The internal diameter of the preferred circular tube is in the millimeter regime, preferably from 0.25 to 1 Mm. The ratio of wall thickness to internal diameter is preferably no more than 0.1 for steel and no more than 0.3 for plastic.

BRIEF DESCRIPTION OF THE DRAWINGS

These and other advantages of the invention will be better understood when the detailed description of the preferred embodiments of the invention is read in conjunction with the drawings, wherein.

DETAILED DESCRIPTION OF THE PREFERRED EMBODIMENTS

Numerical solution of the characteristic equation results in a dispersion equation for axial wave propagation. The axial wave number is complex, the imaginary part being the spatial attenuation coefficient. The frequency is also complex, the imaginary part being the temporal damping coefficient. The frequency dependences of these various factors can be derived and displayed in non-dimensional graphs that are useful in designing ultrasonic waveguides.

Numerically, the dispersion relation exhibits a positive real part and a negative imaginary part, as expected. The former is the wave number, Re[k], for axial propagation of compression waves in the azimuthal mode denoted by the integer n, and the latter is the axial attenuation coefficient, Iz[k], for that mode. The complex wave number is given by the equation:

$$k = \eta \frac{\omega}{c_0} - i \frac{\xi}{RC_0} \sqrt{\frac{v_0 \omega}{2c_0^2}}$$

where the eigenvalues $\eta(R, H, \omega)$ and $\xi(r, H, \omega)$ are solutions of the characteristic equation, written symbolically as:

$$F_N(\omega, \eta, \xi) = 0$$

where $\omega$ is the angular frequency; $c_o$ is the speed of sound in the fluid; $v_o$ is the fluid kinematic viscosity of the first kink; R is the radius of the cylindrical waveguide; and h is the wall thickness of the cylindrical waveguide.

The material and fluid densities, the material elastic properties and the sonic velocities also enter into the numerical solution of the above characteristic equation, which requires a double-iteration technique on a digital computer.

The axi-symmetric mode (n=0) is the mode of interest to the present invention. For metal waveguides, the phase velocity of the wave lies between the sonic velocities for the solid and the fluid and is independent of frequency. On the other hand, as the frequency is increased, the damping increases $\sqrt{\omega}$, all other factors remaining constant. In the case of nonmetal waveguides, more complicated frequency behavior occurs, as will be discussed hereinafter.

Figure 1:
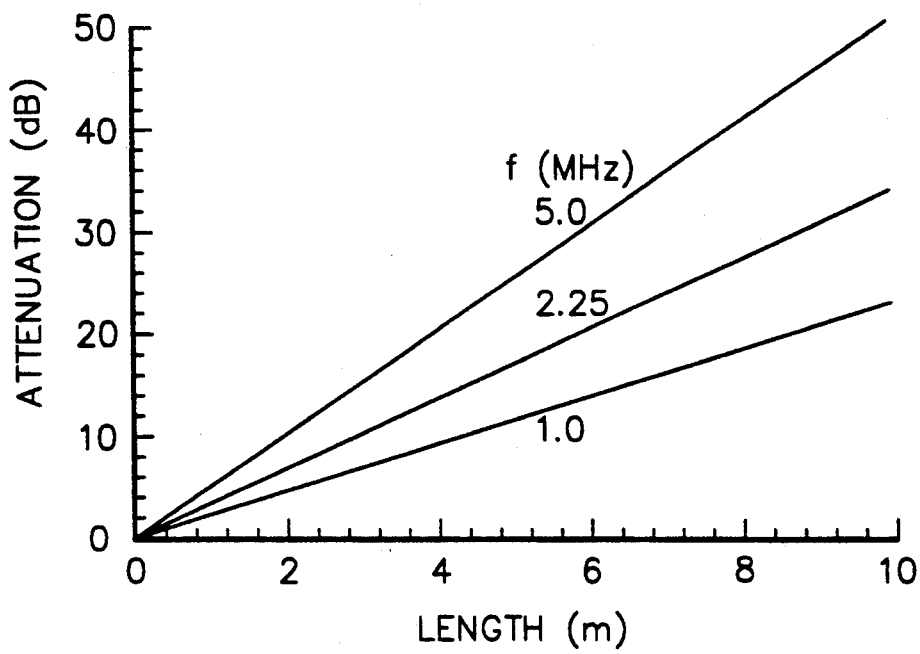
FIGS. 1 and 2 are graphs respectively depicting the amplitude attenuation and phase velocity versus frequency for a water filled steel tube with an internal diameter of 0.51 and a wall thickness of 0.051 mm at 15° C.
Figure 2:
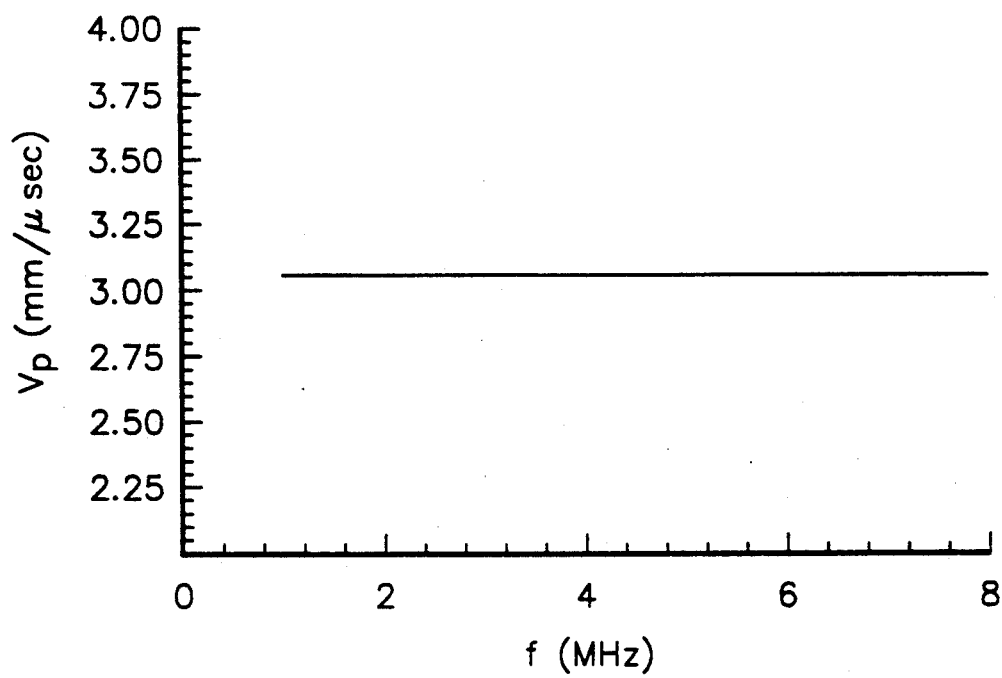

It is convenient to express Re[k·R] and Im[k·R], which are non-dimensional, as a function of the normalized frequency $$\Omega = R\omega \sqrt{\frac{\rho_s(1 - v^2)}{E}}$$

where $\rho_s$ is the material density; E is the material elastic modulus; and $v$ is the material Poison ratio. This results in a universal form of the dispersion equation, from which information about the wave propagation can be obtained. The important parameters derived from this form of the dispersion equation are the phase velocity $V_p$ and amplitude attenuation for a given length of waveguide. The curves in FIGS. 1 and 2 are typical for a steel tube filled with water at 15° C., excited in the n=0 mode. The steel tube for this example has an internal diameter $D_i$ of 0.51 mm and a wall thickness h of 0.051 mm, i.e., $h/D_i=0.1$.

As is evident from FIG. 2, the phase velocity is independent of temperature. The attenuation, on the other hand, is an implicit function of temperature (see FIG. 1), by way of the fluid properties and material thermal expansion. This effect can be shown by defining the attenuation number:

$$Te(\omega,T) = [\sqrt{\pi} \, 20 \log_{10} e] \xi(R,h,\omega) \frac{\sqrt{v_0 f}}{c_0}$$

$$\simeq 15.4 \xi(R,h,\omega) \frac{\sqrt{v_0 f}}{c_0}$$

Figure 3:
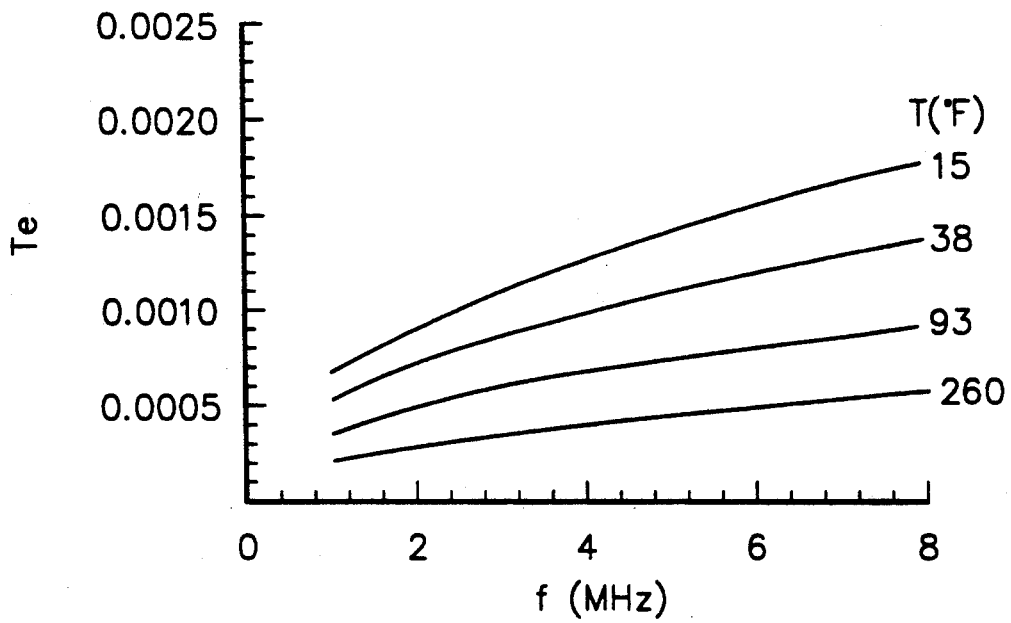
FIG. 3 is a graph depicting the attenuation number versus frequency and temperature for a water-filled steel tube with n internal diameter of 0.51 mm and a wall thickness of 0.051 mm.

The amplitude attenuation in decibels can be derived from the attenuation number as follows:

$$dB_A = Te(\omega,T) \frac{L}{D_i}$$

wherein L and $D_i$ are respectively the length and internal diameter of the tube. Typical values of $T_e$ for a water-filled steel tube having h=0.051 mm and $D_i=0.51$ mm at various temperatures are shown in FIG. 3.

More complicated results are obtained for flexible tubes filled with fluid. The attenuation number versus frequency curve of FIG. 4 and the phase velocity versus frequency curve of FIG. 5 are typical for a polyethylene tube filled with water at 380° C., excited in the n=0 mode. The polyethylene tube for this example has an internal diameter D, of 0.51 mm and a wall thickness h of 0.152 mm, i.e., $h/D_i \approx 0.3$. The wall of the polyethylene tube in this example is thicker than the wall of the steel tube in the previous example, but is made of a flexible plastic material of stiffness much less than that of a steel tube of similar diameter.

Figure 4:
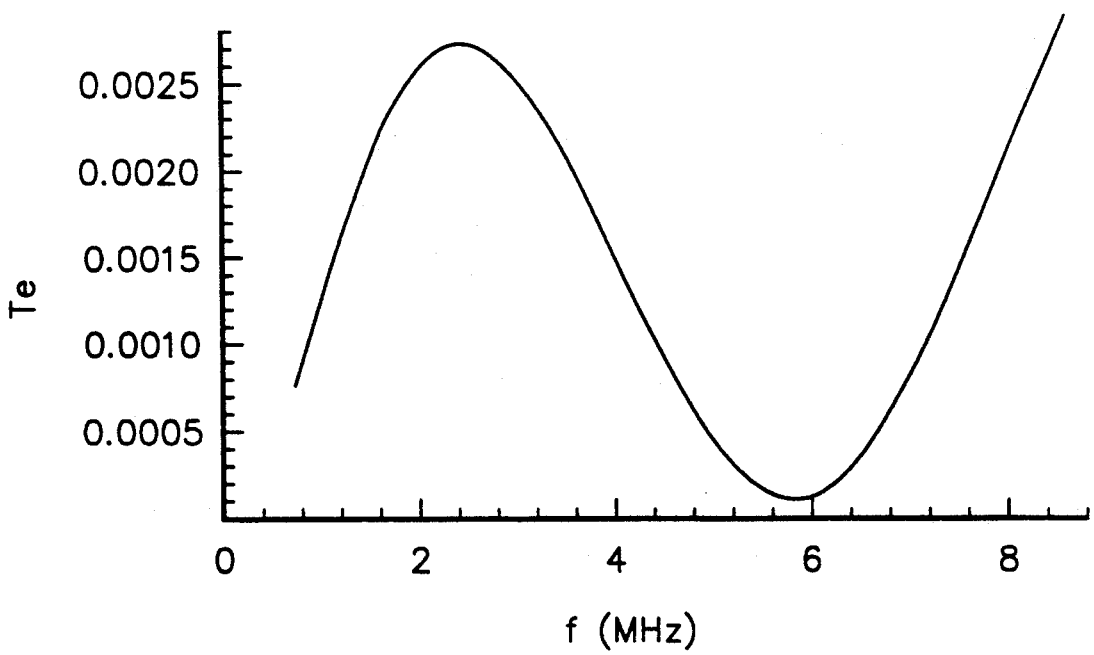
FIGS. 4 through 6 are graphs respectively depicting the attenuation number, amplitude attenuation and phase velocity versus frequency for a water-filled polyethylene tube with an internal diameter of 0.51 Mm and a wall of 0.152 mm at 38° C.
Figure 5:
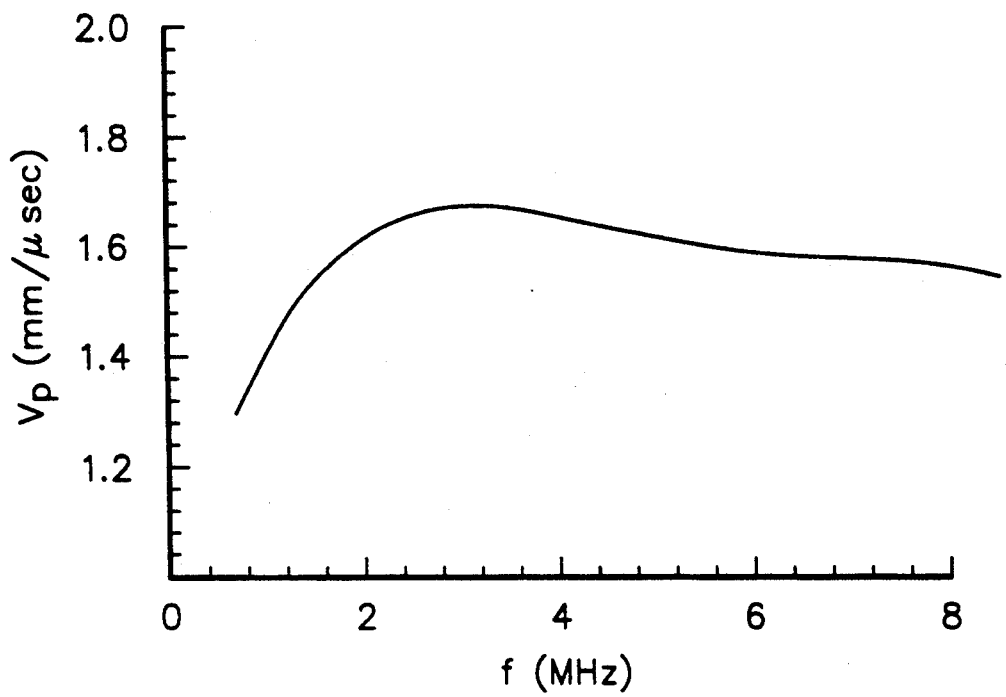

Two properties are apparent f rom the curves of FIGS. 4 and 5. First, the attenuation number is highly variable with frequency. Second, the phase velocity is slightly variable with frequency. In particular, for 2

MHz the propagation is dispersive, whereas for 6 MHz the propagation is non-dispersive. These dependences imply an optimum frequency of application near 6 MHz for this particular combination of material properties and dimensions. Accordingly, it is possible to design a waveguide having minimum attenuation while maintaining nondispersive propagation.

Figure 6:
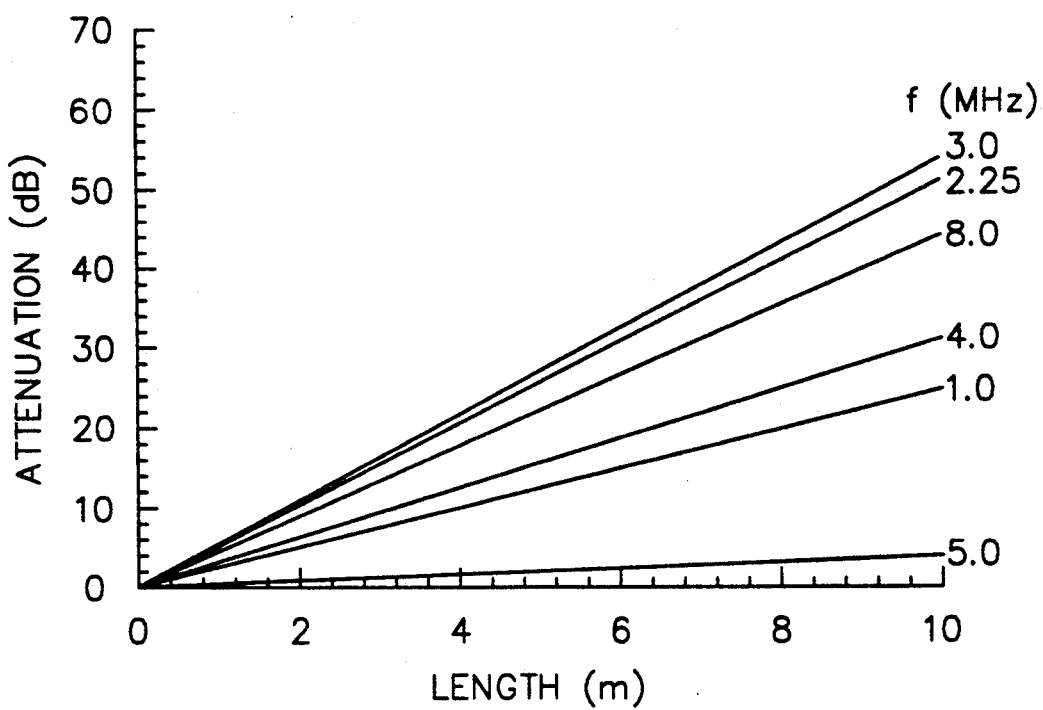

The attenuation of an axially propagating wave in a water-filled polyethylene tube having h=0.152 Mm and $D_i$=0.51 mm at 380° C. for selected frequencies is shown in FIG. 6. Clearly, this design would be a poor choice for frequencies around 3 MHz, but excellent for about 5 MHz.

Figure 7:
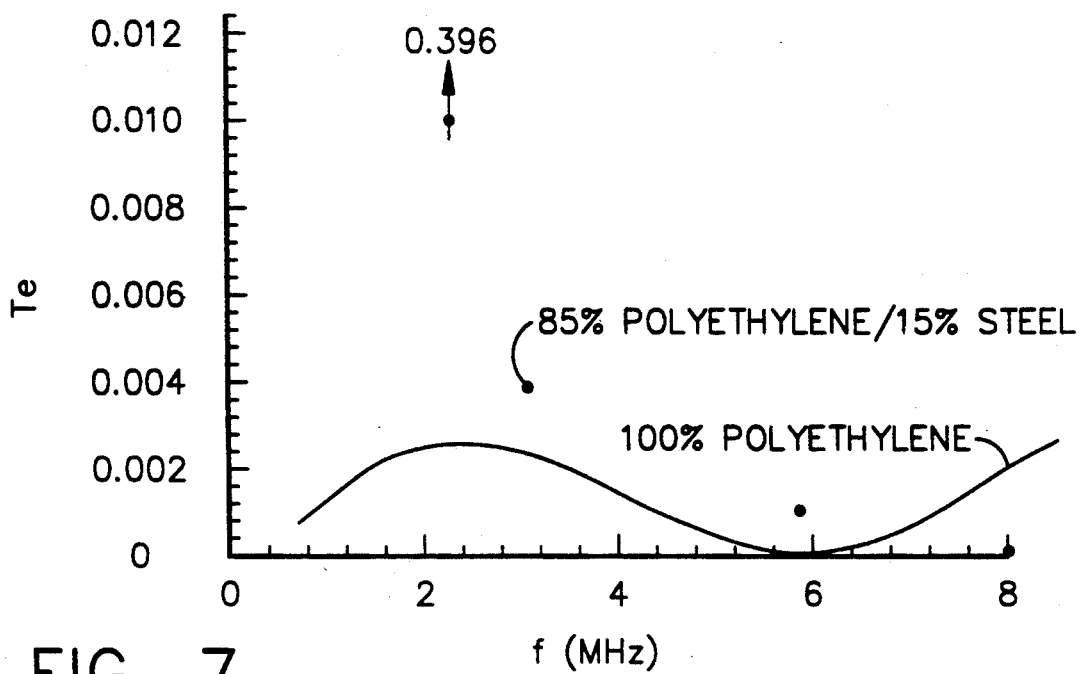
FIG. 7 is a graph depicting the attenuation number versus frequency for a water-filled 100% polyethylene tube and for an 85% polyethylene/15% steel tube at 38° C., both tubes having n internal diameter of 0.51 mm and a wall thickness of 0.152 mm.

A novel aspect of the ultrasonic waveguide of the present invention is the ability to shift the optimum frequency by design. For example, by loading the plastic material with powdered steel during fabrication of the waveguide tube, the effective density of the tube is increased. The effect on attenuation is shown in FIG. 7, which compares the attenuation numbers for waves of four selected frequencies propagating axially in a water-filled 85% polyethylene/15% steel tube with the attenuation number versus frequency curve for a water-filled 100% polyethylene tube at 380° C., both tubes having h=0.152 mm and $D_i$=0.51 mm.

Evidently, the higher density of the composite tube shifts the optimum frequency to around 8 MHz from 6 MHz for the pure material, implying that a less dense material mixture would lower the optimum frequency. Of course, there are other ways to shift the optimum frequency by design, such as by varying the $h/D_i$ ratio, material modulus, or fluid viscosity. A good example is Freon-12 ($CCl_2F_2$), which has a relatively low viscosity at 380° C.

Similar considerations apply to waveguides of rectangular, elliptical or other constant cross section. The numbers differ, but the physical principles are essentially the same as for the circular cylindrical waveguide, which is a preferred configuration. Furthermore, a large number of fluids and solids could be feasibly used in combination. The fluids and solids discussed above are merely exemplary and do not constitute an exclusive list of the materials which can be utilized in the invention.

Figure 8:
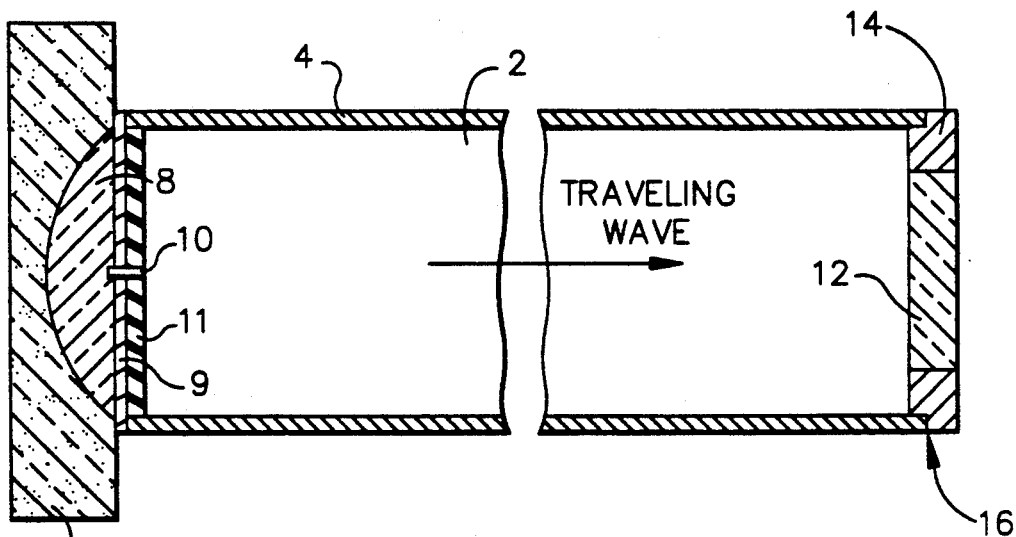
FIG. 8 is a schematic view of an ultrasonic waveguide in accordance with a preferred embodiment of the invention.

The ultrasonic waveguide in accordance with a preferred embodiment of the invention, as shown in FIG. 8, comprises a flexible tube 4 filled with viscous, compressible fluid 2. Tube 4 has a wall with an inner surface which is axisymmetric and of constant cross section. The tube may be made of metal, plastic or metal/plastic composite material.

The fluid 2 in the tube 4 (not shown to scale) is excited at the design frequency by a driving signal imposed on a transducer 6 by external signal generator electronics (not shown). The transducer produces ultrasonic energy which is focused by lens 8. This focused ultrasonic energy excites a metal diaphragm 9 coupled to an exciter pin 10 located at the focus of lens 8. The diaphragm produces an ultrasonic compressional wave with wave number k which enters the waveguide through pin 10 and propagates axially in the fluid. Reverberations and reflections are controlled by the rubber membrane 11 behind the diaphragm 9, which is an efficient absorber of ultrasonic energy.

The traveling wave is a continuous wave, or "burst", which travels along the tube 4 and radiates out a window 12 installed in an end cap 14. End cap 14 closes the opposite end of the tube and is secured to the inner surface of the tube wall by bonding material 16, thereby forming a fluid-tight chamber inside the waveguide. The energy radiated at the exit window 12 is a burst of essentially plane waves, which can be concentrated by a small lens (not shown) near the output, if required by the application. The window material should be made of a material with acoustic impedance close to that of the fluid (e.g., LUCITE for water).

The waveguide in accordance with the invention can operate in the reciprocal mode; that is, a reflection incident on the exit window 12 will propagate through the tube 4, excite the transducer 6 through its contact pin 10 and produce a signal using detection electronics. Therefore, the waveguide can be utilized in the "pulse-echo" mode to remotely place ultrasonic energy of the correct frequency into spaces difficult to access, since its lateral dimension is selected to be small.

A wedge, or "shoe", of appropriate material can be used in place of the exit window to produce refracted waves in material media, if required by the application. In this case, reflected energy from the material is refracted back into the waveguide window and detected as a plane wave incident on pin 10. The method of operation is the same as though the transducer were in contact with the surface itself.

Figure 9:
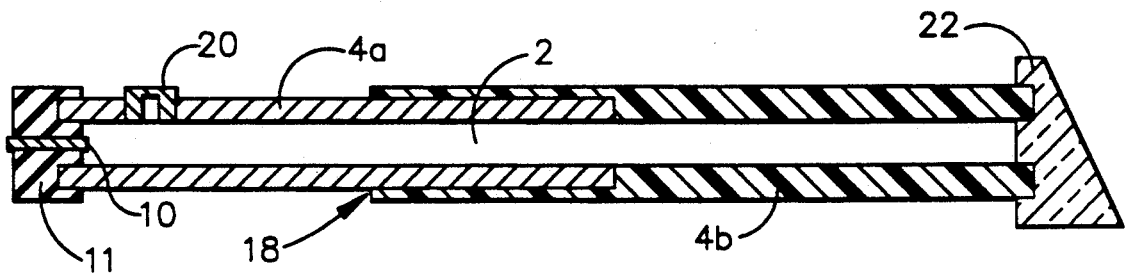
FIG. 9 is a schematic view of a compound ultrasonic waveguide with a refracting "shoe" in accordance with another preferred embodiment of the invention.

Another preferred embodiment, depicted in FIG. 9, has a compound tube comprising a tube portion 4a made of steel and a tube portion 4b made of polyethylene. Both tube portions have cylindrical channels of identical cross section (preferably circular), so that when tube portions 4a and 4b are joined by suitable bonding material 18, a channel having a cross section which is constant throughout the waveguide length is formed. The compound tube is closed off at both ends to form a fluid-tight volume: by rubber membrane 11 at one end and by plastic refracting wedge 22 at the other end. The fluid-tight channel is evacuated and back-filled with viscous, compressible fluid 2 by way of port 20, which is sealed after back-filling.

The traveling wave is launched from exciter pin 10, which is coupled to the transducer (not shown) . The single excitation pin 10 is chosen so that only the axisymmetric mode is excited. Higher-order azimuthal modes are to be avoided by design. Typically, the pin is less than 0.1 mm in diameter.

The refracting wedge is coupled to the end of the tube which is remote from exciter pin 10. Wedge 22 refracts the propagating ultrasonic wave as it exits the waveguide.

Such a compound waveguide is advantageous in situations where the waveguide must satisfy different requirements in different sections along its length. For example, the polyethylene tube is more flexible than the steel tube. Another difference is that, for some frequencies and temperatures, attenuation is greater for wave propagation inside a fluid-filled polyethylene tube than it is for wave propagation inside a fluid-filled steel tube. Therefore, it would be advantageous to use steel tubing for straight sections and polyethylene tubing for bends or turns in the waveguide for those temperatures and frequencies. A practitioner skilled in ultrasonic detection will recognize that a compound waveguide can be optimally designed by joining tubing made of other metals, plastic and composites thereof having desired properties.

The length of the waveguide in accordance with the invention is dictated by the application. The maximum waveguide length is dictated by the amount of attenuation due to viscous dissipation as waves propagate along the waveguide. The outer diameter is typically about 1 mm. The wall dimensions must be carefully machined over several meters. Depending on the material, the wall thickness need be only a fraction of a millimeter. If the wall thickness is nonuniform, then reflections and losses result.

For the 6 MHz case with 380° C. water in a steel tube, the attenuation loss is quite acceptable for a short length. The polyethylene tube displays much less attenuation with 38° C. water, i.e., about 2 dB/m of length. Therefore, substantial distances can be traversed with losses easily compensated by electronic amplification, if necessary.

Some applications are amenable to the use of liquid metals, such as mercury, whose kinematic viscosity is roughly 10% of the value for water at the same temperature. This can reduce the attenuation, but requires a metal-walled waveguide due to the high density of mercury. The selection of the fluid medium depends on the type of application and whether unusually long distances must be traversed by the waveguide.

The foregoing preferred embodiments have been disclosed only to illustrate the broad concept of the invention. It will be obvious to the skilled practitioner that the tube materials and compressible fluids used, the dimensions of the tube, and the temperature all can be varied to optimize the performance of the waveguide of the invention for a specific frequency of ultrasonic waves.

I claim:

1. An ultrasonic waveguide comprising:
    tubular wall means having a channel of substantially constant cross section formed therein and having first and second open ends;
    first and second fluid-tight sealing means connected to said tubular wall means for respectively closing said first and second open ends to make said channel fluid-tight; and
    a viscous, compressible fluid medium filling said fluid-tight channel,
    wherein said first and second fluid-tight sealing means respectively comprise first and second coupling means for allowing ultrasonic waves to propagate axially into and out of said fluid medium at said ends of said channel, said fluid medium and the dimensions and material of said tubular wall means being selected such that the eigenvalues $\eta$ and $\xi$ satisfy a characteristic equation $F_n(\omega, \eta, \xi)=0$ resulting from the coupling at the interface between said tubular wall means and said fluid.

2. The ultrasonic waveguide as defined in claim 1, wherein said wall means comprises metal.

3. The ultrasonic waveguide as defined in claim 1, wherein said wall means comprises plastic material.

4. The ultrasonic waveguide as defined in claim 1, wherein said wall means comprises plastic material loaded with metal particles.

5. The ultrasonic waveguide as defined in claim 1, wherein said channel is cylindrical.

6. The ultrasonic waveguide as defined in claim 5, wherein said channel has circular cross section.

7. The ultrasonic waveguide as defined in claim 1, wherein said wall means comprises a first tubular section made of a first material and a second tubular section made of a second material, said first and second materials being different in composition.

8. The ultrasonic waveguide as defined in claim 7, wherein said first material comprises metal and said second material comprises plastic material.

9. The ultrasonic waveguide as defined in claim 8, wherein said metal is steel and said plastic material is polyethylene.

10. The ultrasonic waveguide as defined in claim 1, further comprising transducing means coupled to said first coupling means for transforming electrical energy into ultrasonic vibrations which are transmitted by said first coupling means down said channel as ultrasonic waves propagating in a first direction and for transforming ultrasonic vibrations in said first coupling means into electrical energy, said vibrations in said first coupling means resulting from the propagation of ultrasonic waves along said channel in a second direction, said second direction being opposite to said first direction.

11. The ultrasonic waveguide as defined in claim 10, wherein said second coupling means comprises means for refracting said ultrasonic waves propagating in said first direction after said waves leave said fluid medium.

12. A system for transmitting ultrasonic waves from a first location to a second location, comprising:
    tubular wall means having a channel of substantially constant cross section formed therein and having first and second open ends;
    first and second fluid-tight sealing means connected to said tubular wall means for respectively closing said first and second open ends to make said channel fluid-tight; and
    a viscous, compressible fluid medium filling said fluid-tight channel,
    wherein said first fluid-tight sealing means comprises transducing means for transforming electrical energy into ultrasonic waves which propagate down said channel in a first direction and for transforming ultrasonic waves which propagate down said channel in a second direction into electrical energy, said second fluid-tight sealing means comprises coupling means for allowing ultrasonic waves to propagate axially into and out of said fluid medium at said ends of said channel, said fluid medium and the dimensions and material of said tubular wall means being selected such that the eigenvalues $\eta$ and $\xi$ satisfy a characteristic equation $F_n(\omega, \eta, \xi)=0$ resulting from the coupling at the interface between said tubular wall means and said fluid.

13. The system as defined in claim 12, wherein said coupling means comprises means for refracting said ultrasonic waves propagating in said first direction after said waves leave said fluid medium.

14. The system as defined in claim 12, wherein said tubular wall means comprises metal.

15. The system as defined in claim 12, wherein said tubular wall means comprises plastic material.

16. The system as defined in claim 12, wherein said tubular wall means comprises plastic material loaded with metal particles.

17. The system as defined in claim 12, wherein said channel is circular cylindrical.

18. The system as defined in claim 12, wherein said wall means comprises a first tubular section made of a first material and a second tubular section made of a second material, said first and second materials being different in composition.

19. The system as defined in claim 18, wherein said first material comprises metal and said second material comprises plastic material.

20. A method for transmitting ultrasonic waves from a first location to a second location using a waveguide, comprising the steps of:

forming a tubular wall having a channel of substantially constant cross section formed therein and having first and second open ends respectively situated at said first and second locations, said channel having an axis of propagation;

closing said first and second open ends to make said channel fluid-tight;

filling said fluid-tight channel with a viscous, compressible fluid medium;

transmitting ultrasonic waves from said first closed end along said axis of propagation of said fluid-tight channel;

guiding said transmitted ultrasonic waves to impinge on said second closed end; and transmitting said ultrasonic waves through said second closed end so that said ultrasonic waves exit said fluid-tight channel into the volume external to said waveguide, said fluid medium and the dimensions and material of said tubular wall means being selected such that the eigenvalues $\eta$ and $\xi$ satisfy a characteristic equation $F_n(\omega, \eta, \xi)=0$ resulting from the coupling at the interface between said tubular wall means and said fluid.

* * * * *